(12) United States Patent
Little

(10) Patent No.: US 9,650,595 B2
(45) Date of Patent: May 16, 2017

(54) QUATERNARY AMMONIUM HYDROXIDES

(71) Applicant: SACHEM, Inc., Austin, TX (US)

(72) Inventor: Charles B. Little, Austin, TX (US)

(73) Assignee: Sachem, Inc., Austin, TX (US)

( * ) Notice: Subject to any disclaimer, the term of this patent is extended or adjusted under 35 U.S.C. 154(b) by 124 days.

(21) Appl. No.: 14/808,560

(22) Filed: Jul. 24, 2015

(65) Prior Publication Data

US 2015/0329475 A1 Nov. 19, 2015

Related U.S. Application Data

(62) Division of application No. 13/430,985, filed on Mar. 27, 2012, now Pat. No. 9,090,859.

(51) Int. Cl.

| | |
|---|---|
| C11D 7/50 | (2006.01) |
| C07C 215/40 | (2006.01) |
| C07D 295/088 | (2006.01) |
| C07C 217/28 | (2006.01) |
| C11D 3/28 | (2006.01) |
| C11D 3/30 | (2006.01) |
| C11D 3/43 | (2006.01) |
| C11D 7/32 | (2006.01) |
| C11D 1/62 | (2006.01) |

(52) U.S. Cl.
CPC .......... *C11D 7/5004* (2013.01); *C07C 215/40* (2013.01); *C07C 217/28* (2013.01); *C07D 295/088* (2013.01); *C11D 3/28* (2013.01); *C11D 3/30* (2013.01); *C11D 3/43* (2013.01); *C11D 7/3209* (2013.01); *C11D 7/3218* (2013.01); *C11D 7/3227* (2013.01); *C11D 7/3281* (2013.01); *C07C 2101/04* (2013.01); *C11D 1/62* (2013.01)

(58) Field of Classification Search
CPC ........... C07C 217/28; C11D 1/62; C11D 3/28; C11D 3/30
See application file for complete search history.

(56) References Cited

U.S. PATENT DOCUMENTS

| | | |
|---|---|---|
| 5,259,888 A | 11/1993 | McCoy |
| 5,780,406 A | 7/1998 | Honda et al. |
| 5,962,383 A | 10/1999 | Doyel et al. |
| 2007/0051627 A1 | 3/2007 | Niinobe et al. |
| 2012/0263903 A1 | 10/2012 | Varma et al. |

OTHER PUBLICATIONS

Beckett M A et al; "A 11 B NMR study of zwitterionic and cationic monoborate complexes with cationic 1,2-diol ligands", Polyhedron, vol. 27, No. 9-10, Jun. 26, 2008, pp. 2226-2230.

S.M. Gawish et al; "Synthesis of a New Cationic Surfactant for the Alkaline Hydrolysis of Solvent-Pretreated Polyester Fabrics", Journal of Applied Polymer Science, vol. 85, 2002, pp. 1652-1660.

P.P. Salvi et al; "An efficient protocol for synthesis of tetrahydrobenzo[b]pyrans using amino functionalized ionic liquid", Comptes Rendus Chimie, vol. 14, 2011, pp. 878-882.

PCT/US2013/030100; PCT International Search Report and Written Opinion of the International Searching Authority dated May 29, 2013.

SciFinder search results, search carried out on SciFinder by Applicant, on Jul. 16, 2015.

*Primary Examiner* — Gregory Webb

(74) *Attorney, Agent, or Firm* — Renner, Otto, Boisselle & Sklar, LLP

(57) ABSTRACT

A composition including (a) a quaternary ammonium hydroxide having a general formula (I):

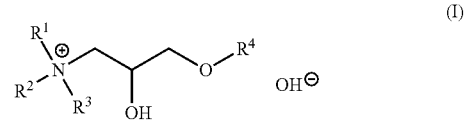

as defined herein, and (b) a dipolar aprotic solvent substantially free of water.

4 Claims, No Drawings

QUATERNARY AMMONIUM HYDROXIDES

CROSS-REFERENCE TO RELATED APPLICATION

The present application is a division of and claims priority under 35 U.S.C. §120 to U.S. application Ser. No. 13/430,985, filed on 27 Mar. 2012, and issued as U.S. Pat. No. 9,090,859 on 28 Jul. 2015, the entirety of which is hereby incorporated herein by reference.

TECHNICAL FIELD

The present invention relates to new quaternary ammonium compounds, in particular to new quaternary ammonium hydroxides for use in strippers and cleaners, particularly in the semiconductor processing industry, but also in any industry in which a thorough cleaning of hard-to-remove organic-based contaminants is needed.

BACKGROUND

Highly specialized organic polymers are used in many capacities as surface coatings in the manufacture of electronic devices. These polymer coatings may be permanent features of the finished product, but more often they are temporary coatings meant to serve as protective and/or sacrificial barriers. For example, in the manufacture of a logic device, a suitably reactive polymer, usually an electromagnetic radiation-reactive polymer may be used as a photoresist in a microlithography step to construct transistors or interconnects. Such polymers may also be referred to as photodefinable materials or as photoimageable materials.

In each instance in which the polymer is used as a protective or sacrificial coating, the polymer-coated surface is likely to be subjected to conditions so harsh that the nature of the polymer is profoundly changed, leaving ill-defined organic/inorganic surface residues. These residues must then be removed before the next step in the manufacturing process.

The polymer as initially applied may have been substantially soluble in many organic solvents. For instance, most photoresist polymers are designed to be soluble in such organic solvents as ethyl lactate, from which solution a thin layer of polymer is applied by spin-coating and solvent evaporation.

Thin polymer films applied by spin-coating solutions in organic solvents are easily removed by rinsing with the solvents used in the spin-coating process. The universe of solvents that may be used to remove spin-coated polymer films is not limited to the solvents used in the spin-coating process. For example, a thin film of a common Novolac-based photoresist, Megaposit™ SPR™220 from Dow Electronic Materials, applied by spin-coating an ethyl lactate solution, may be removed completely by rinsing with acetone or methanol from a solvent wash bottle.

However, after the polymer film has been subjected to a harsh processing step, such as a high-temperature bake, plasma etching or high-energy and/or high-dose ion implantation, the organic/inorganic material that remains is rarely soluble in any known organic solvent. For example, as is known in the art, polymers exposed to heat will cure to a higher extent due the formation of a surface skin, which results from accelerated curing from the heat, and higher bulk density at the surface. The polymer skin is more difficult to remove. As another example, high energy or high dose ion implantation can result in 3D crosslinking of the polymer, again resulting in much more difficulty in removal of the residue. In many cases, the only effective method of removing these residues consists of applying organic solvents that contain a strongly alkaline component. However, prior art compositions have been less than satisfactory for a variety of reasons.

Accordingly, a need remains for more effective cleaning agents to remove such difficult-to-remove residues.

SUMMARY

The present invention provides a solution to the problem of developing more effective cleaning agents to remove such difficult to remove residues.

In one embodiment, the present invention relates to a method of removing a residue from a surface, including:
applying to the surface a composition comprising:
(a) a quaternary ammonium hydroxide having a general formula (I):

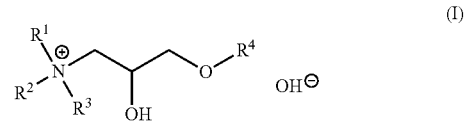

wherein in the general formula (I):
$R^1$ may be $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen,

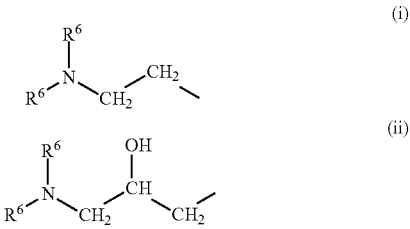

or $R^1$ may have the following general formulae (i) or (ii):
wherein in general formulae (i) and (ii), $R^6$ is independently $C_1$-$C_4$ branched or unbranched alkyl,
$R^2$ and $R^3$ may be independently $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or
$R^1$ is as defined above, and $R^2$ and $R^3$ may together form a heterocyclic ring containing the quaternary ammonium N atom of the general formula (I) and 4 to 7 carbon atoms, or
$R^1$ is as defined above, and $R^2$ and $R^3$ may together form a heterocyclic ring containing the quaternary ammonium nitrogen atom of the general formula (I), and either a second nitrogen atom or an oxygen atom and 3 to 6 carbon atoms, wherein the second nitrogen atom may be substituted with one or two groups independently selected from $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$, $R^2$, and $R^3$ together may form a bicyclic structure containing from two to four carbon atoms between first and second bridgehead positions, wherein the quaternary N atom of the general formula (I) is at the first bridgehead position, and a carbon or a tertiary or quaternary nitrogen is at the second bridgehead position, wherein when the second bridgehead position is a carbon or a quaternary nitrogen, the carbon or quaternary nitrogen is substituted with $R^5$, in which $R^5$ is H or a $C_1$-$C_4$ branched or unbranched alkyl group, and $R^4$ is H or $C_1$-$C_{18}$ linear or branched alkyl, phenyl or substituted phenyl, or benzyl or substituted benzyl, wherein when present, substituted phenyl or substituted benzyl is substituted with one or more of $C_1$-$C_4$ alkyl, $C_1$-$C_4$ alkoxy, or halogen; and (b) a dipolar aprotic solvent substantially free of water; and removing at least a substantial portion of the residue from the surface.

In one embodiment, the present invention relates to a composition of matter, wherein the composition comprises:

a quaternary ammonium hydroxide having a general formula (I):

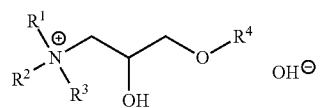

(I)

wherein in the general formula (I):

$R^1$ may be $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$ may have the following general formulae (i) or (ii):

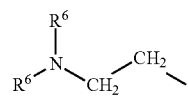

(i)

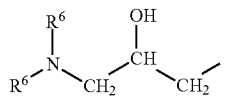

(ii)

wherein in general formulae (i) and (ii), $R^6$ is independently $C_1$-$C_4$ branched or unbranched alkyl, $R^2$ and $R^3$ may be independently $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$ is as defined above, and $R^2$ and $R^3$ may together form a heterocyclic ring containing the quaternary ammonium N atom of the general formula (I) and 4 to 7 carbon atoms, or $R^1$ is as defined above, and $R^2$ and $R^3$ may together form a heterocyclic ring containing the quaternary ammonium nitrogen atom of the general formula (I), and either a second nitrogen atom or an oxygen atom and 3 to 6 carbon atoms, wherein the second nitrogen atom may be substituted with one or two groups independently selected from $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$, $R^2$, and $R^3$ together may form a bicyclic structure containing from two to four carbon atoms between first and second bridgehead positions, wherein the quaternary N atom of the general formula (I) is at the first bridgehead position, and a carbon or a tertiary or quaternary nitrogen is at the second bridgehead position, wherein when the second bridgehead position is a carbon or a quaternary nitrogen, the carbon or quaternary nitrogen is substituted with $R^5$, in which $R^5$ is H or a $C_1$-$C_4$ branched or unbranched alkyl group, and $R^4$ is H or $C_1$-$C_{18}$ linear or branched alkyl, phenyl or substituted phenyl, or benzyl or substituted benzyl, wherein when present, substituted phenyl or substituted benzyl is substituted with one or more of $C_1$-$C_4$ alkyl, $C_1$-$C_4$ alkoxy, or halogen, with the provisos that, if $R^4$ is H, then all of $R^1$, $R^2$ and $R^3$ are not any combination of methyl and ethyl groups; if $R^4$ is H and $R^1$ and $R^2$ are methyl, then if $R^3$ is benzyl, it is substituted benzyl; if $R^4$ is mono-substituted phenyl, the substituent is other than a 4-fluoro or a 4-alkyl group; and if $R^4$ is di-substituted phenyl, the di-substituted phenyl is other than 2,5-dimethylphenyl.

In one embodiment, the quaternary ammonium hydroxide has one of the following structures:

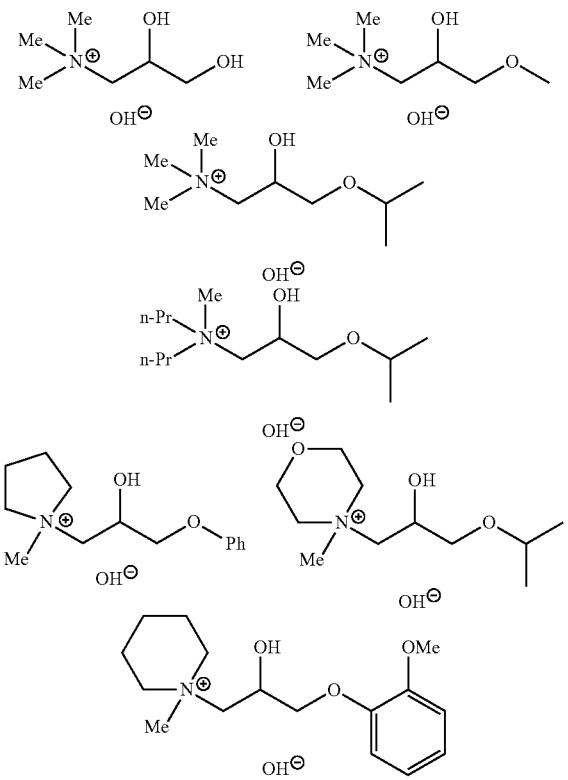

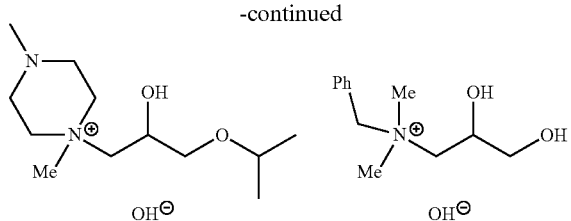

based on the general formula (I).

In one embodiment, the quaternary ammonium hydroxide has general formula (II):

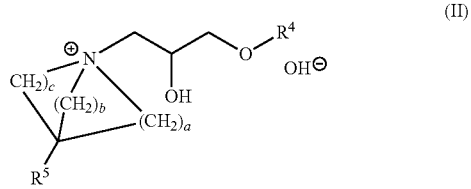

wherein, in general formula (II), each of a, b and c are independently 2-4, $R^5$ is H or a $C_1$-$C_4$ branched or unbranched alkyl.

In one embodiment, the quaternary ammonium hydroxide has general formula (III):

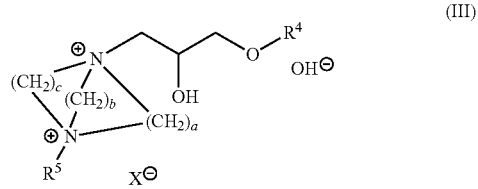

wherein, in general formula (III), each of a, b and c are independently 2-4, $R^5$ is a $C_1$-$C_4$ branched or unbranched alkyl, and X is a halide or OH.

In one embodiment, the quaternary ammonium hydroxide has general formula (IV):

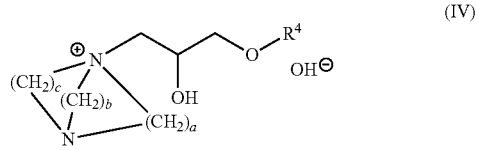

wherein in general formula (IV), each of a, b and c are independently 2-4.

In one embodiment, the dipolar aprotic solvent includes one or more of dimethylsulfoxide (DMSO), dimethylsulfone, N-methylpyrrolidinone (NMP), N-ethylpyrrolidinone (NEP), pyridine, acetone, ethyl acetate, dimethyl acetamide, tetramethylene sulfone, nitrobenzene, dimethyl carbonate, diethyl carbonate, ethylene carbonate, propylene carbonate, tetramethyl urea, acetonitrile, propionitrile, hexamethylphosphoramide, piperylene sulfone, N-methylmorpholine oxide, sulfolane, gamma-butyrolactone and dimethylformamide (DMF).

In one embodiment, the composition further comprises one or a mixture of two or more of a surfactant, a corrosion inhibitor, and a metal chelating agent.

In one embodiment, the surfactant comprises one or a mixture of any two or more of an anionic surfactant, a cationic surfactant, a nonionic surfactant, a fluoroalkyl surfactant, polyethylene glycols, polypropylene glycols, polyethylene glycol ethers, polypropylene glycol ethers, carboxylic acid salts, dodecylbenzene sulfonic acid or salts thereof, polyacrylate polymers, silicone or modified silicone polymers, acetylenic diols or modified acetylenic diols, alkylammonium or modified alkylammonium salts.

In one embodiment, the corrosion inhibitor comprises one or a mixture of any two or more of catechol; $C_1$-$C_6$ alkylcatechols, phenols, pyrogallol, benzotriazole; $C_1$-$C_{10}$ alkylbenzotriazoles, formic acid, acetic acid, propionic acid, butyric acid, isobutyric acid, oxalic acid, malonic acid, succinic acid, glutaric acid, maleic acid, fumaric acid, benzoic acid, phthalic acid, 1,2,3-benzenetricarboxylic acid, glycolic acid, lactic acid, malic acid, citric acid, acetic anhydride, phthalic anhydride, maleic anhydride, succinic anhydride, salicylic acid, gallic acid, organic salts of the foregoing organic acids, wherein the organic salt comprises one or more of ethanolamine, trimethylamine, diethylamine and aminopyridines, methyl gallate, propyl gallate, ethanolamine, trimethylamine, diethylamine and pyridines, such as 2-aminopyridine, phosphoric acid-based chelate compounds, 1,2-propanediaminetetramethylene phosphonic acid and hydroxyethane phosphonic acid, ethylenediaminetetraacetic acid and its sodium and ammonium salts, dihydroxyethylglycine and nitrilotriacetic acid, bipyridine, tetraphenylporphyrin, phenanthroline, dimethylglyoxime and diphenylglyoxime.

In one embodiment, the metal chelating agent comprises one or a mixture of any two or more of (ethylenedinitrilo) tetraacetic acid (EDTA), terpyridine, citric acid, gluconic acid, gallic acid, pyrogallol, salicylaldoxime, 8-hydroxyquinoline, polyalkylenepolyamines, crown ethers, oxalic acid, maleic acid, malonic acid, malic acid, tartaric acid, aspartic acid, benzoic acid, gluconic acid, glycolic acid, succinic acid, salts of the aforementioned acids, acetylacetone, glycine, dithiocarbamates, amidoximes, catechol, and cysteine.

In one embodiment, the residue comprises one or more of a post-bake residue from a polymeric material, an at least partially decomposed polymeric material, a residue derived from a photoresist, and a spin-on dielectric material.

In one embodiment, the surface is a component of a semiconductor device in a manufacturing process.

The foregoing compounds according to formula (I), and the method of removing a residue from a surface using these compounds, provides a novel and unexpectedly excellent method of removing such residues. The present invention thereby provides a solution to the long-standing problem of providing such a versatile and wide-ranging method for removal of hard-to-remove residues, and to the long-felt need for compositions that are particularly effective in removing such residues, while at the same time avoiding the need to use protic solvents and/or water to obtain solubilization of the quaternary ammonium compounds for use in removing such residues from surfaces. The methods and compositions in accordance with the present invention are particularly effective for removing residues such as one or more of a post-bake residue from a polymeric material, an ion-implanted polymeric material, a partially decomposed polymeric material, a residue derived from a photoresist, and a spin-on dielectric material.

DETAILED DESCRIPTION

The present invention provides a powerful new composition for removing such residues as are created in harsh processing steps, such as a high-temperature bake, plasma etching or high-energy and/or high-dose ion implantation in, e.g., fabrication of a semiconductor device.

As used herein, a dipolar aprotic (DA) solvent is a solvent with a comparatively high relative permittivity (or dielectric constant), e.g., greater than about 15, and a sizable permanent dipole moment, and which cannot donate suitably labile hydrogen atoms to form strong hydrogen bonds.

As used herein, "substantially free of water" means that the composition so described contains no purposely added water, and contains water in an amount less than about 0.1% by weight, based on the whole composition. In one embodiment, the dipolar aprotic solvent substantially free of water contains less than about 0.05% by weight of water, based on the whole composition. In one embodiment, the dipolar aprotic solvent substantially free of water contains less than about 0.01% by weight of water, based on the whole composition.

Throughout the disclosure and claims, the numerical limits of the disclosed ranges and ratios may be combined, and all intervening values are deemed to be disclosed by the disclosure of the ranges. All numerical ranges are inclusive and combinable in any order, except where it is clear that such numerical ranges are constrained to add up to 100%. Furthermore, all numerical values are deemed to be preceded by the modifier "about", whether or not this term is specifically stated. Throughout the disclosure and claims, any member of a group may be deleted from the group. Throughout the disclosure and claims, all possible combinations of the various disclosed elements may be combined, and all such combinations are considered to be disclosed within the scope of the present disclosure, which should be readily understood by the skilled person. Unless otherwise specified, all temperatures are measured in degrees Celsius, all processes are conducted at room or ambient temperature, all pressures are atmospheric.

It is to be understood that unless specifically stated otherwise, reference to "a", "an", and/or "the" may include one or more than one, and that reference to an item in the singular may also include the item in the plural, except where it is clear that only one is intended.

As used throughout this specification, the following abbreviations shall have the following meanings, unless the context clearly indicates otherwise: % wt=weight percent; μm=micron=micrometer; nm=nanometer; ° C.=degrees Celsius; sec.=second; min.=minute; Å=angstrom; ca.=approximately; mL=milliliter; DI=deionized; and rpm=revolutions per minute.

The terms "resin" and "polymer" are used interchangeably throughout this specification. "Polymer" includes homopolymers and copolymers.

Where compounds within the scope of the present invention include enantiomers or other isomeric forms, all enantiomers, both as racemic forms (±) and as separate enantiomers (+) and (−), are contemplated. Racemic forms can be resolved into the optical antipodes by known methods and techniques. For example, diastereomeric salts may be resolved by use of an optically active acid, and liberating the optically active amine compound by treatment with a base. Alternatively, the resolution may be based on chromatographic methods in which an optically active matrix is used. Racemic compounds of the present invention can thus be resolved by fractional crystallization of d- or l-(tartrate, mandelate, or camphorsulfonate) salts, for example. Additional methods for resolving optical isomers are known in the art, and include methods described by Collet, et al. in "*Enantiomers, Racemates and Resolutions*", John Wiley and Sons, New York (1981).

Because of their strong solvent power, dipolar-aprotic (DA) solvents are especially advantageous in stripper and cleaner formulations. Typical DA organic solvents used in stripper and cleaner formulations today are dimethylsulfoxide (DMSO) and N-methylpyrrolidine (NMP). Suitable DA solvents include one or more of dimethylsulfoxide (DMSO), dimethylsulfone, N-methylpyrrolidinone (NMP), N-ethylpyrrolidinone (NEP), pyridine, acetone, ethyl acetate, dimethyl acetamide, tetramethylene sulfone, nitrobenzene, dimethyl carbonate, diethyl carbonate, ethylene carbonate, propylene carbonate, tetramethyl urea, acetonitrile, propionitrile, hexamethylphosphoramide, piperylene sulfone, N-methylmorpholine oxide, sulfolane, gamma-butyrolactone and dimethylformamide (DMF). In one embodiment, the DA solvent consists essentially of one or a combination of two or more of the foregoing DA solvents. In one embodiment, the DA solvent consists of one or a combination of two or more of the foregoing DA solvents.

Inorganic bases, such as NaOH and KOH, have limited solubility in pure DA organic solvents, but are sometimes used when a miscible, protic co-solvent can be included to increase the solubility. Protic co-solvents include 1,2-ethanediol, 1,2-propanediol, monoethanolamine and the like. Because these DA solvents are miscible with water, the protic co-solvent may also be water.

Quaternary ammonium hydroxides offer an advantage over inorganic bases because (among other things) they are more soluble in these DA solvents. TMAH is the quaternary ammonium hydroxide most often used in commercial formulations of strippers and cleaners. However, there are at least two known deficiencies of TMAH that plague formulators of these products:

1) Water content. The stable, commercial form of TMAH that contains the least water is the solid pentahydrate (TMAH.5H$_2$O, or abbreviated TMAH-P). Thus, introduction of a certain amount of water is unavoidable when using TMAH in a stripper or cleaner formulation. Such formulations can be desiccated, as in US patent application 2010/0104824 (to Dynaloy). But desiccation of stripper and cleaner formulations to remove some of the water introduced with TMAH-P is highly impractical. However, using TMAH-P to increase base content, one must necessarily increase water content. This inability to vary independently the concentration of base and water severely limits the flexibility of a formulator.

2) Solubility. Despite its organic nature, TMAH-P is not very soluble in pure DA solvents. TMAH-P is more soluble than inorganic bases, but not nearly as soluble as is often required for optimal performance as a stripper or cleaner. For example, TMAH-P is only soluble to the extent of about 2.5 wt % in pure DMSO. Since TMAH-P is almost exactly 50 wt % water, the actual concentration of TMAH in solution is <1.3 wt %. Effective cleaning formulations in this solvent typically contain 5 wt % TMAH (or more), equivalent to an OH$^-$ concentration of approximately 0.55 mol/kg (or more). To achieve this concentration of base, the use of protic co-solvents is required. This poses a dilemma to formulators. Protic co-solvents (e.g., ethylene glycol) are known to have a detrimental effect on cleaning, so the advantage gained in increasing TMAH concentration must be balanced against the advantage lost in using a protic co-solvent to achieve the high TMAH concentration.

The present invention does not suffer from the foregoing disadvantages of TMAH.

The present inventor has discovered that a particular class of quaternary ammonium hydroxides provides a unique solution to these problems. The class includes quaternary ammonium compounds having the structure according to general formula (I):

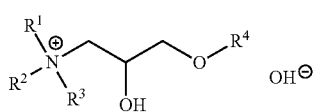
(I)

wherein in the general formula (I):

$R^1$ may be $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$ may have the following general formulae (i) or (ii):

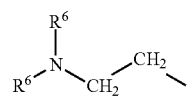
(i)

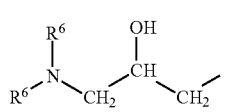
(ii)

wherein in general formulae (i) and (ii), $R^6$ is independently $C_1$-$C_4$ branched or unbranched alkyl, $R^2$ and $R^3$ may be independently $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$ is as defined above, and $R^2$ and $R^3$ may together form a heterocyclic ring containing the quaternary ammonium N atom of the general formula (I) and 4 to 7 carbon atoms, or $R^1$ is as defined above, and $R^2$ and $R^3$ may together form a heterocyclic ring containing the quaternary ammonium nitrogen atom of the general formula (I), and either a second nitrogen atom or an oxygen atom and 3 to 6 carbon atoms, wherein the second nitrogen atom may be substituted with one or two groups independently selected from $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$, $R^2$, and $R^3$ together may form a bicyclic structure containing from two to four carbon atoms between first and second bridgehead positions, wherein the quaternary N atom of the general formula (I) is at the first bridgehead position, and a carbon or a tertiary or quaternary nitrogen is at the second bridgehead position, wherein when the second bridgehead position is a carbon or a quaternary nitrogen, the carbon or quaternary nitrogen is substituted with $R^5$, in which $R^5$ is H or a $C_1$-$C_4$ branched or unbranched alkyl group, and $R^4$ is H or $C_1$-$C_{18}$ linear or branched alkyl, phenyl or substituted phenyl, or benzyl or substituted benzyl, wherein when present, substituted phenyl or substituted benzyl is substituted with one or more of $C_1$-$C_4$ alkyl, $C_1$-$C_4$ alkoxy, or halogen.

In the method according to various embodiments of the present invention, the quaternary ammonium compounds of formula (I) are generally used with one or a combination of two or more DA solvent substantially free of water, as defined above.

In one embodiment, the present invention relates to a method of removing a residue from a surface, comprising
 applying to the surface a composition comprising:
 (a) the quaternary ammonium hydroxide having the general formula (I) as defined above, and
 (b) a dipolar aprotic (DA) solvent substantially free of water; and
 removing at least a substantial portion of the residue from the surface.

In one embodiment, the present invention relates to a composition of matter, wherein the composition comprises:
 a quaternary ammonium hydroxide having a general formula (I):

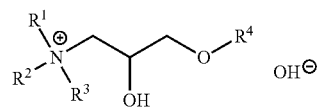
(I)

wherein in the general formula (I):

$R^1$ may be $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$ may have the following general formulae (i) or (ii):

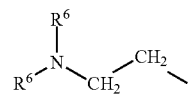
(i)

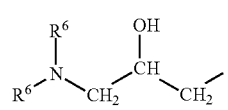
(ii)

wherein in general formulae (i) and (ii), $R^6$ is independently $C_1$-$C_4$ branched or unbranched alkyl, $R^2$ and $R^3$ may be independently $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$ is as defined above, and $R^2$ and $R^3$ may together form a heterocyclic ring containing the quaternary ammonium N atom of the general formula (I) and 4 to 7 carbon atoms, or $R^1$ is as defined above, and $R^2$ and $R^3$ may together form a heterocyclic ring containing the quaternary ammonium nitrogen atom of the general formula (I), and either a second nitrogen atom or an oxygen atom and 3 to 6 carbon atoms, wherein the second nitrogen atom may be substituted with one or two groups independently selected from $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$, $R^2$, and $R^3$ together may form a bicyclic structure containing from two to four carbon atoms between first and second bridgehead positions, wherein the quaternary N atom of the general formula (I) is at the first bridgehead position, and a carbon or a tertiary or quaternary nitrogen is at the second bridgehead position, wherein when the second bridgehead position is a carbon or a quaternary nitrogen, the carbon or quaternary nitrogen is substituted with $R^5$, in which $R^5$ is H or a $C_1$-$C_4$ branched or unbranched alkyl group, and $R^4$ is H or $C_1$-$C_{18}$ linear or branched alkyl, phenyl or substituted phenyl, or benzyl or substituted benzyl, wherein when present, substituted phenyl or substituted benzyl is substituted with one or more of $C_1$-$C_4$ alkyl, $C_1$-$C_4$ alkoxy, or halogen, with the provisos that, if $R^4$ is H, then all of $R^1$, $R^2$ and $R^3$ are not any combination of methyl and ethyl groups; if $R^4$ is H and $R^1$ and $R^2$ are methyl, then if $R^3$ is benzyl, it is substituted benzyl; if $R^4$ is mono-substituted phenyl, the substituent is other than a 4-fluoro or a 4-alkyl group; and if $R^4$ is di-substituted phenyl, the di-substituted phenyl is other than 2,5-dimethylphenyl.

The foregoing provisos with respect to $R^4$ are intended to exclude all known compounds from the scope of the compositions of matter disclosed herein. With respect to the methods disclosed herein, none of the disclosed quaternary ammonium hydroxides are known or have been suggested for use in such methods.

In one embodiment, the quaternary ammonium hydroxide has one of the following structures:

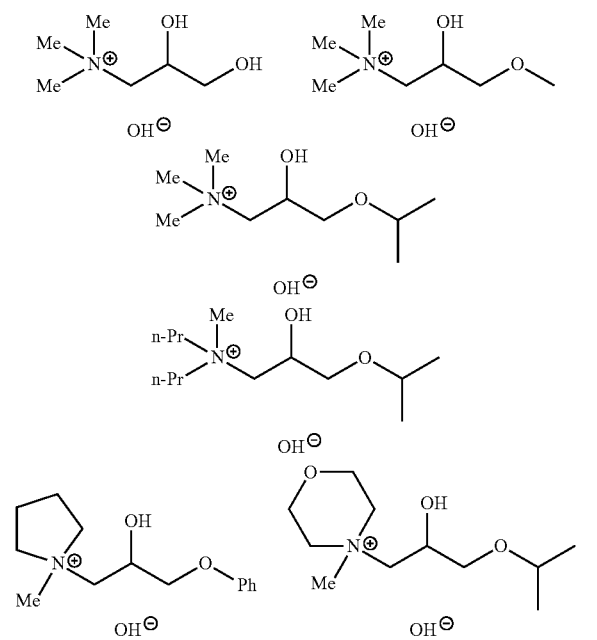

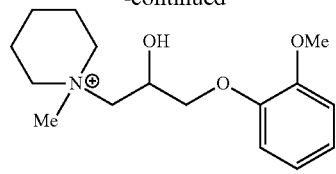

all of which are based on the general formula (I).

In one embodiment, in the general formula (I), when $R^1$ has the following general formulae (i) or (ii):

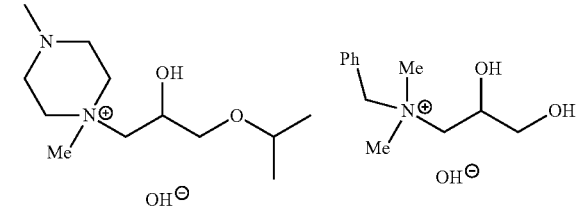

in which $R^6$ is independently $C_1$-$C_4$ branched or unbranched alkyl, the resulting quaternary ammonium hydroxide has one of the two general formulae:

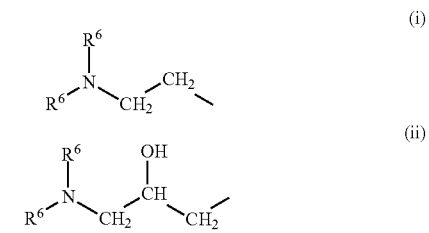

wherein $R^2$, $R^3$ and $R^4$ are as defined above.

In one embodiment, as described above, $R^1$ is as defined above, and $R^2$ and $R^3$ may together form a heterocyclic ring containing the quaternary ammonium N atom of the general formula (I) and 4 to 7 carbon atoms. The following structures, including some of those shown above, are examples of this embodiment, all of which are based on the general formula (I).

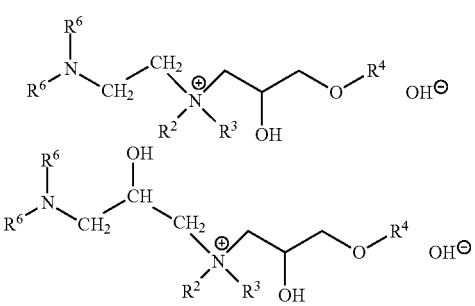

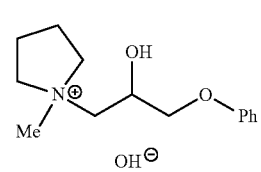

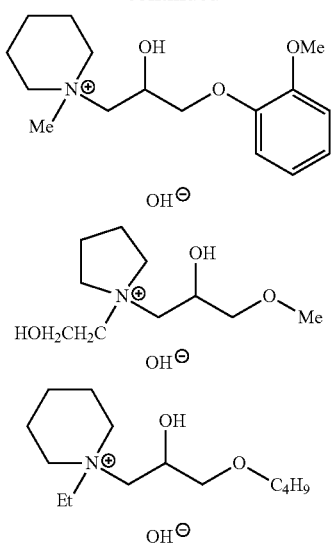

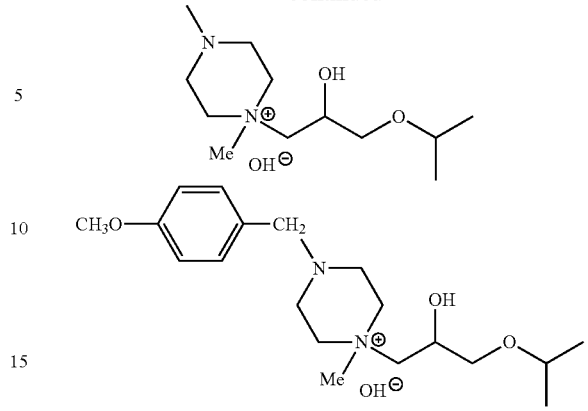

In one embodiment, as described above, $R^1$ is as defined above, and $R^2$ and $R^3$ may together form a heterocyclic ring containing the quaternary ammonium nitrogen atom of the general formula (I), and either a second nitrogen atom or an oxygen atom and 3 to 6 carbon atoms. In this embodiment, the second nitrogen atom may be substituted with one or two groups independently selected from $C_1$-$C_{18}$ linear or branched alkyl, $C_2$-$C_{18}$ linear or branched alkanol, $C_3$-$C_{18}$ linear or branched polyol, benzyl, or substituted benzyl. When present, substituted phenyl or substituted benzyl is substituted with one or more of $C_1$-$C_4$ alkyl, $C_1$-$C_4$ alkoxy, or halogen. The following structures, including some of those shown above, are examples of this embodiment, all of which are based on the general formula (I).

In one embodiment, as described above, $R^1$, $R^2$, and $R^3$ together may form a bicyclic structure containing from two to four carbon atoms between first and second bridgehead positions, wherein the quaternary N atom in formula (I) is at the first bridgehead position, and a carbon, or a tertiary or quaternary nitrogen is at the second bridgehead position, wherein when the second bridgehead position is a carbon or a quaternary nitrogen, the carbon or quaternary nitrogen is substituted with $R^5$, in which $R^5$ is H or a $C_1$-$C_4$ branched or unbranched alkyl group.

In certain of these bicyclic embodiments, the compound is a quaternary azabicyclo[a,b,c]alkane, wherein the quaternary nitrogen atom is at the first bridgehead position, and each of a, b and c are independently 2-4, and the second bridgehead atom is carbon, substituted with $R^5$, wherein $R^5$ is H, a $C_1$-$C_4$ branched or unbranched alkyl. Thus, for example, the following general formula (II) is within the scope of this embodiment:

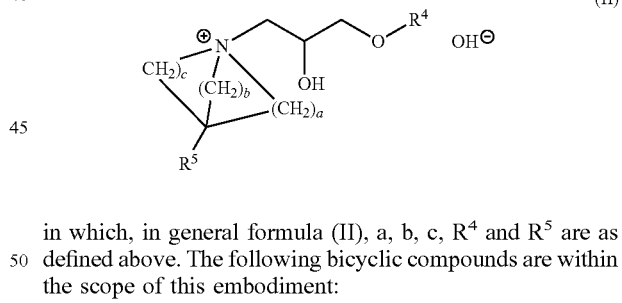

(II)

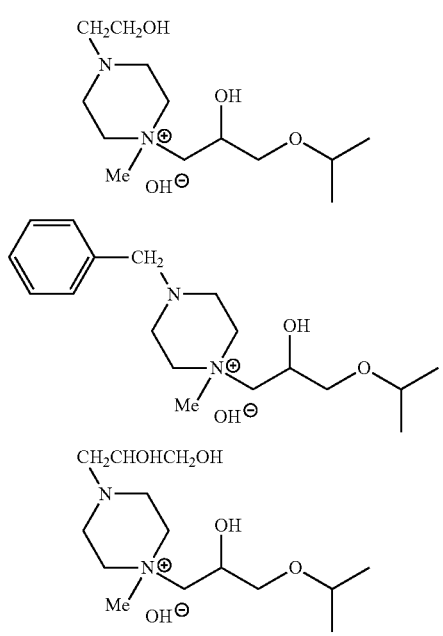

in which, in general formula (II), a, b, c, $R^4$ and $R^5$ are as defined above. The following bicyclic compounds are within the scope of this embodiment:

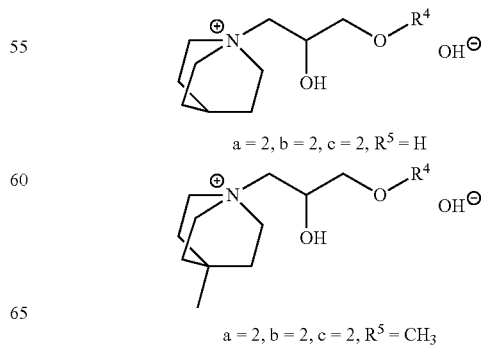

a = 2, b = 2, c = 2, $R^5$ = H a = 2, b = 2, c = 2, $R^5$ = $CH_3$

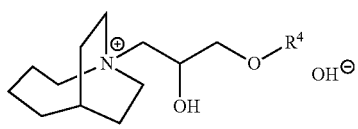

a = 2, b = 2, c = 4, R⁵ = H

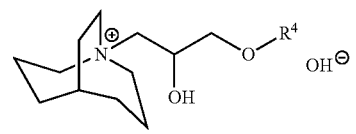

a = 3, b = 2, c = 3, R⁵ = H

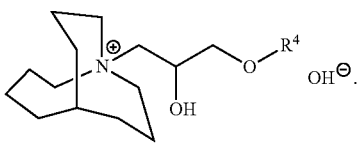

a = 3, b = 3, c = 4, R⁵ = H

In certain of these bicyclic embodiments, the compound is a quaternary diazabicyclo[a,b,c]alkane, wherein the quaternary nitrogen atom is at the first bridgehead position, and each of a, b and c are independently 2-4, and the second bridgehead atom is a nitrogen atom which may be substituted or unsubstituted and which, when substituted, is substituted with $R^5$, wherein $R^5$ is a $C_1$-$C_4$ branched or unbranched alkyl group, thus forming a second quaternary nitrogen atom. Thus, for example, the following general formulae (III) and (IV) are within the scope of this embodiment:

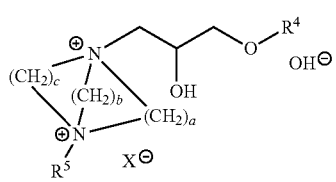

(III)

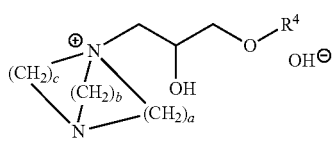

(IV)

wherein in general formula (III), each of a, b, c, $R^4$ and $R^5$ are as defined above, and X is a halide or a second OH group, and in general formula (IV) each of a, b and c are as defined above. The following bicyclic compounds are within the scope of this embodiment:

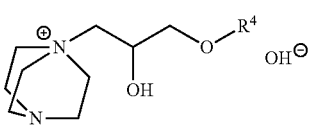

a = 2, b = 2, c = 2, R⁵ = H

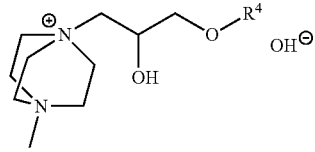

a = 2, b = 2, c = 2, R⁵ = CH₃

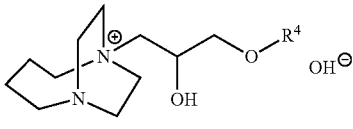

a = 2, b = 2, c = 4, R⁵ = H

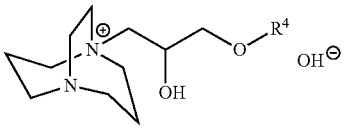

a = 3, b = 2, c = 3, R⁵ = H

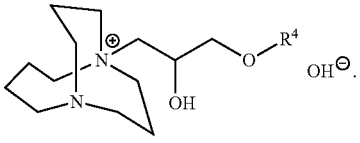

a = 3, b = 3, c = 4, R⁵ = H

As will be recognized, in the foregoing monoquaternary ammonium embodiments, substitution of the second nitrogen atom with a fourth substituent, i.e., $R^5$, as defined above, would form the corresponding diquaternary ammonium compounds.

It is further noted that, in either of the two bicyclic embodiments described above, if any one of a, b or c is zero, then the resulting compound is within the description of the mono-heterocyclic embodiment, in which $R^2$ and $R^3$ form a heterocyclic ring containing the quaternary ammonium N atom.

The foregoing bicyclic structures are merely exemplary; the foregoing description provides a sufficiently detailed description of the bicyclic compounds within the scope of the present invention, such that a person of skill in the art can readily appreciate both the variations within the scope of the description and how to make the various compounds within the scope of the description.

In one embodiment, the residue comprises one or more of a post-bake residue from a polymeric material, an ion-implanted polymeric material, a partially decomposed polymeric material, a residue derived from a photoresist, and a spin-on dielectric material. In one embodiment, the polymeric material or photoresist may include, but are not limited to, photoresists and photoimageable dielectric materials. In general, such photodefinable materials contain a binder polymer, a cross-linking agent and a photoactive component, such as a photoacid or photobase generator, and may contain additional components to improve the patterned image. Typically, the photoresists are positive-acting and may contain a variety of compositions. Exemplary photoresists may contain novolac resins, poly(hydroxystyrene) resins, acrylate or (meth)acrylate resins, cyclic olefin resins, siloxane resins, silsesquioxane resins, and the like, as well as mixtures thereof. Particularly suitable photoresists include those containing one or more novolac resins, such as mixed isomer cresol/formaldehyde novolacs, phenol/formaldehyde novolacs, mixed isomer cresol/phenol/formaldehyde novolacs and the like, silsesquioxane resins, acrylate or (meth) acrylate resins and cyclic olefin resins. Particularly suitable photodefinable materials are silicon-containing photoresists, and more particularly photoresists containing silsesquioxane-containing binder polymers. Such photoresists may be chemically amplified. Suitable photoresists are sold by Dow Electronic Materials. In the case of a wafer used in the manufacture of an integrated circuit, the photoresist is generally spin coated onto the wafer to provide a layer having a desired thickness. A residue derived from a photoresist is a residue that may contain developed or undeveloped photoresist, a degradation product of a photoresist, e.g., a photoresist that has been exposed to one or more ion implantation, high temperature or chemical or physical degradation.

Suitable thicknesses of the polymeric material layer are up to about 5 μm, or in some embodiments, up to 2 μm and in some embodiments, up to 1 μm. Typically, the photoresist layer has a minimum thickness of 0.1 μm, although thinner layers may be advantageously used, as known in the art.

The polymeric material may be coated on the substrate by any conventional technique, such as screen coating (or screen printing), curtain coating, roller coating, slot coating, spin coating, flood coating, electrostatic spray, spray coating, dip coating and as a dry film. Spin coating is usually preferred. Such coating techniques are well known to those skilled in the art.

The following general process for forming the photoresist or other material based on the polymeric material is provided as a non-limiting example. Such processes are known in the art, and may differ from the following exemplary process. Once the polymeric material composition has been applied to form a layer of photodefinable material on the substrate surface, the polymeric material layer is "softbaked". The polymeric material layer is next imaged through a mask using actinic radiation of the appropriate wavelength for the photoresist, such as 248 nm, 193 nm, 157 nm, EUV, e-beam, and the like. Imaging of a positive-acting photoresist renders the imaged areas more soluble than the non-imaged areas of the photoresist.

The imaged photodefinable material layer is next developed to form a patterned polymeric material. Such development removes the areas rendered more soluble during imaging of the positive-acting polymeric material and may be achieved through the use of certain organic solvents or dilute alkaline compositions. Suitable developers are generally commercially available. Of course, if the polymeric material is a negative-acting material, the opposite material will be rendered more soluble.

It is the steps that follow in the processing, in which the photoresist or other polymeric material is exposed to high heat, irradiation, ion implantation, etc., that gives rise to the difficult-to-remove material that is the material to be removed according to embodiments of the present invention.

In one embodiment, the surface is a component of a semiconductor device in a manufacturing process.

In one embodiment, the composition further comprises one or a mixture of two or more of a surfactant, a corrosion inhibitor, and a metal chelating agent.

A surfactant may be added in order to assist in both the lifting-off of insoluble photoresist residues and to reduce silicon etching, which may occur under exposure to strong bases. Suitable surfactants include, but are not limited to, anionic, cationic, nonionic surfactants, such as fluoroalkyl surfactants, polyethylene glycols, polypropylene glycols, polyethylene or polypropylene glycol ethers, carboxylic acid salts, dodecylbenzene sulfonic acid or salts thereof, polyacrylate polymers, silicone or modified silicone polymers, acetylenic diols or modified acetylenic diols, alkylammonium or modified alkylammonium salts, as well as combinations comprising at least one of the foregoing surfactants. Surfactants may be useful at levels ranging from about 0.001% wt to about 2% wt, based on the total weight of the composition.

Suitable corrosion inhibitors include, but are not limited to, aromatic hydroxyl compounds such as catechol; $C_1$-$C_6$ alkylcatechols such as methylcatechol, ethylcatechol and t-butylcatechol, phenols and pyrogallol; aromatic triazoles such as benzotriazole; $C_1$-$C_{10}$ alkylbenzotriazoles; carboxylic acids such as formic acid, acetic acid, propionic acid, butyric acid, isobutyric acid, oxalic acid, malonic acid, succinic acid, glutaric acid, maleic acid, fumaric acid, benzoic acid, phthalic acid, 1,2,3-benzenetricarboxylic acid, glycolic acid, lactic acid, malic acid, citric acid, acetic anhydride, phthalic anhydride, maleic anhydride, succinic anhydride, salicylic acid, gallic acid, and gallic acid esters such as methyl gallate and propyl gallate; organic salts of carboxyl containing organic containing compounds described above, basic substances such as ethanolamine, trimethylamine, diethylamine and pyridines, such as 2-aminopyridine, and the like, and chelate compounds such as phosphoric acid-based chelate compounds including 1,2-propanediaminetetramethylene phosphonic acid and hydroxyethane phosphonic acid, carboxylic acid-based chelate compounds such as ethylenediaminetetraacetic acid and its sodium and ammonium salts, dihydroxyethylglycine and nitrilotriacetic acid, amine-based chelate compounds such as bipyridine, tetraphenylporphyrin and phenanthroline, and oxime-based chelate compounds such as dimethylglyoxime and diphenylglyoxime. A single corrosion inhibitor may be used or a combination of any two or more of the foregoing corrosion inhibitors may be used. Corrosion inhibitors may be useful at levels ranging from about 1 ppm to about 10% wt, based on the total weight of the composition.

Suitable metal chelating agents include, but are not limited to, (ethylenedinitrilo)tetraacetic acid (EDTA), terpyridine, citric acid, gluconic acid, gallic acid, pyrogallol, oximes such as salicylaldoxime, 8-hydroxyquinoline, polyalkylenepolyamines, crown ethers, oxalic acid, maleic acid, malonic acid, malic acid, tartaric acid, aspartic acid, benzoic acid, gluconic acid, glycolic acid, succinic acid, salts of the aforementioned acids or mixtures of the acids or their salts, acetylacetone, glycine, dithiocarbamates, amidoximes, catechol, and cysteine. The metal chelating agents are typically present in amounts of 500 ppm to 10 wt %, based on the total weight of the solution. In other embodiments, the metal chelating agents may be present in amounts of 1 to 7.5 wt % or 1.5 to 5 wt %, based on the total weight of the composition.

In one embodiment, a single compound is added to function as both corrosion inhibitor and metal chelating agent, such as catechol, EDTA, gallic acid, etc., as can be suitably selected from the foregoing by the person skilled in the art.

In one embodiment, the composition of the present invention is free of added alkanolamine. In one embodiment, the composition of the present invention is substantially free of alkanolamine. Free of added alkanolamine means that no alkanolamine is purposely added. Substantially free of alkanolamine means that no alkanolamine is purposely added and any alkanolamine present is present as an unavoidable impurity in some other purposely added component.

In one embodiment, the composition consists essentially of components (a) and (b). In one embodiment, the composition consists essentially of components (a) and (b), together with one or a mixture of two or more of a surfactant, a corrosion inhibitor, and a metal chelating agent. In one embodiment, the composition consists essentially of components (a) and (b), together with one or a mixture of two or more surfactants. In one embodiment, the composition consists essentially of components (a) and (b), together with one or a mixture of two or more corrosion inhibitors. In one embodiment, the composition consists essentially of components (a) and (b), together with one or a mixture of two or more metal chelating agents. In one embodiment, the composition consists essentially of components (a) and (b), together with one or a mixture of two or more of a surfactant and a corrosion inhibitor. In one embodiment, the composition consists essentially of components (a) and (b), together with one or a mixture of two or more of a surfactant and a metal chelating agent. In one embodiment, the composition consists essentially of components (a) and (b), together with one or a mixture of two or more of a corrosion inhibitor and a metal chelating agent.

Preparation of Exemplary Quaternary Ammonium Hydroxides

The synthetic routes to these compounds should be straightforward for anyone skilled in the art of organic synthesis. These methods include but are not limited to (1) reaction between a tertiary amine and an oxirane, as exemplified by the industrial synthesis of choline hydroxide, as disclosed in U.S. Pat. No. 2,774,759:

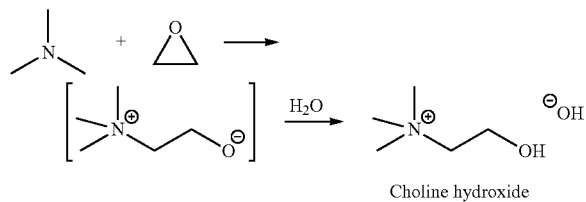

Choline hydroxide or (2) by metathesis from a quaternary ammonium halide:

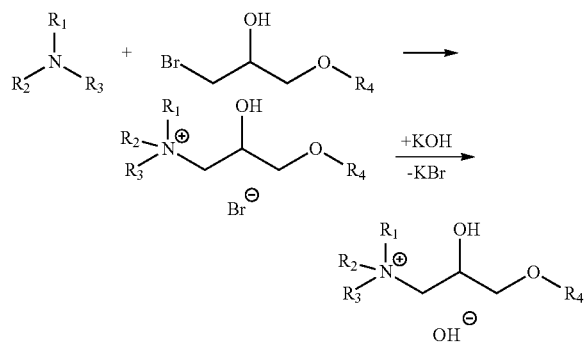

or (3) by electrodialysis from a quaternary ammonium halide.

These quaternary ammonium hydroxides may be obtained in substantially dry form, but are readily soluble in DA solvents without the use of protic co-solvents. Furthermore, they are effective replacements for TMAH as the source of hydroxide in formulations intended as strippers and cleaners, as described herein.

EXAMPLE 1

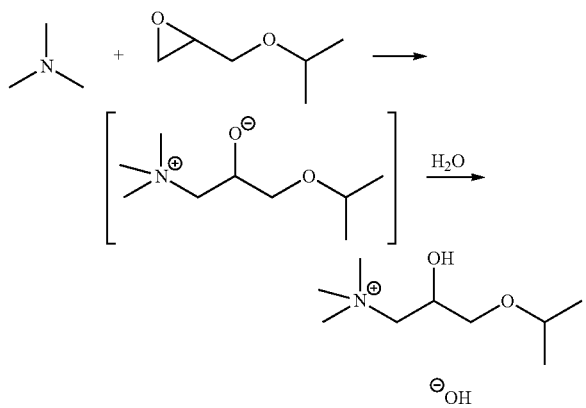

Into a polypropylene reaction vessel is weighed 59.06 g of a 25 wt % solution of trimethylamine in methanol (0.250 moles trimethylamine). To this solution is added 14.50 g isopropylglycidyl ether (0.125 moles) by syringe under a nitrogen atmosphere with vigorous stirring (Teflon coated magnetic stir bar). Soon after the addition of the glycidyl ether to the amine solution is started, a strong exotherm is noted. With the aid of a syringe pump the rate of addition is adjusted to keep the internal temperature less than approximately 10° C. above ambient. When addition of the glycidyl ether is complete, the temperature slowly begins to drop. The solution is stirred for an additional 30 minutes, during which time the internal temperature drops approximately 4° C.

At this point, the internal temperature is still above ambient. A methanol solution containing 6.76 g $H_2O$ (0.375 moles, 15 mL total volume) is added by syringe at such a rate that the temperature remains steady rather than continuing to fall to ambient. When this addition is complete (approximately 30 minutes) the vessel is placed in a constant temperature water bath. Approximately one hour is allowed for the internal temperature to stabilize to 25° C. The solution is then purged with dry nitrogen gas delivered by Teflon needle submerged below the liquid surface. Purging is continued until the purge gas fails to register a color change in wet pH paper, signaling that substantially all excess trimethylamine has been removed. Some methanol may evaporate during the nitrogen purging step, so fresh methanol is added as needed to bring the total mass up to 100 g. The targeted hydroxide concentration is 1.25 mol/kg, and the concentration actually found by titration is about 1.17 mol/kg.

The quaternary ammonium hydroxide of this Example is a new composition of matter. Its structure may be confirmed by conversion to a neutral halide salt. Thus, a small portion of the methanol solution of the quaternary ammonium hydroxide is neutralized with a slight excess of 48% aqueous HBr, volatiles are removed, and the solid residue is recrystallized from methyl ethyl ketone (MEK) to yield a white crystalline solid (>99.6% purity by HPLC). The $^1$H-NMR and $^{13}$C-NMR spectra ($D_2O$, TPS reference) are consistent with the assigned structure.

EXAMPLE 2

A portion of the methanol solution obtained in Example 1 (approximately 7.5 g, containing $8.8 \times 10^{-3}$ moles of the quaternary ammonium hydroxide) in a 50 mL polypropylene centrifuge tube is evaporated under a stream of dry nitrogen to a viscous oil. The tube containing this viscous oil is placed in a vacuum chamber and held for 5 hours at <$10^{-2}$ mm Hg, during which time the viscous oil solidifies as the last traces of solvent are removed.

Pure DMSO (12.84 g) is added to the tube immediately upon its removal from the vacuum chamber, the cap is tightly secured and the contents of the tube gently agitated. After less than 5 minutes all solids dissolve to yield a clear, colorless solution. Analysis of this solution by titration reveal an OH$^-$ concentration of 0.54 mol/kg (target 0.58 mol/kg). Water content by Karl-Fischer titration is zero. This dry, concentrated solution is effective in removing the residue from a Novolac photoresist from wafer coupons, after the photoresist had been baked at 155° C. for 4 hours. Under the same conditions, pure DMSO is found to be ineffective in removing this baked Novolac film.

EXAMPLE 3

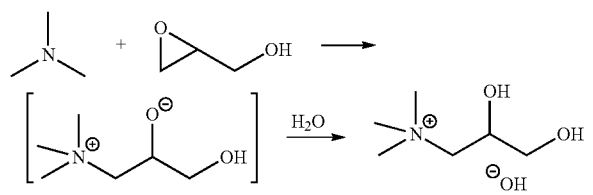

Substantially the same procedure outlined in Example 1 is repeated, with the following two modifications: (1) glycidol is used instead of the glycidyl ether, and (2) the glycidol, being much more viscous than the glycidyl ether, is diluted with methanol rather than used neat in order to facilitate addition by syringe. Targeted hydroxide concentration is 1.00 mol/kg, and the concentration actually found by titration is 1.00 mol/kg.

The quaternary ammonium hydroxide of this Example is not a new composition of matter. Its preparation, by a method similar to that described here, has been reported by Beckett, et. al. (Polyhedron, vol. 27, pp 2226-2230, 2008). As a further check on the present method, the hydroxide is neutralized with 48% aqueous HBr, volatiles removed and the crude quaternary ammonium bromide recrystallized from IPA. The purified quaternary ammonium bromide has physical and spectral properties identical with literature values for material prepared by alkylation of trimethylamine by 3-bromo-1,2-propanediol (Jaeger, et. al., J. Am. Chem. Soc., 111, pp. 3001-3006, 1989).

EXAMPLE 4

A portion of the methanol solution obtained in Example 3 (approximately 7.4 g, containing 7.4×$10^{-3}$ moles of the quaternary ammonium hydroxide) in a 50 mL polypropylene centrifuge tube is evaporated under a stream of dry nitrogen to a viscous oil. The tube containing this viscous oil is placed in a vacuum chamber and held for 2 hours at <$10^{-2}$ mm Hg, during which time the last traces of solvent are removed. The initially mobile, viscous oil becomes immobile, but does not solidify.

Pure DMSO (13.34 g) is added to the tube immediately upon its removal from the vacuum chamber, the cap is tightly secured and the contents of the tube gently agitated. After less than 5 minutes all solids dissolve to yield a clear, colorless solution. Analysis of this solution by titration reveals an OH$^-$ concentration of 0.50 mol/kg (target 0.50 mol/kg). Water content by Karl-Fischer titration is 0.06 wt %.

This dry, concentrated solution is effective in removing Novolac photoresist from wafer coupons that have been baked at 155° C. for 4 hours. Under the same conditions, pure DMSO is found to be ineffective in removing this baked Novolac film.

EXAMPLE 5

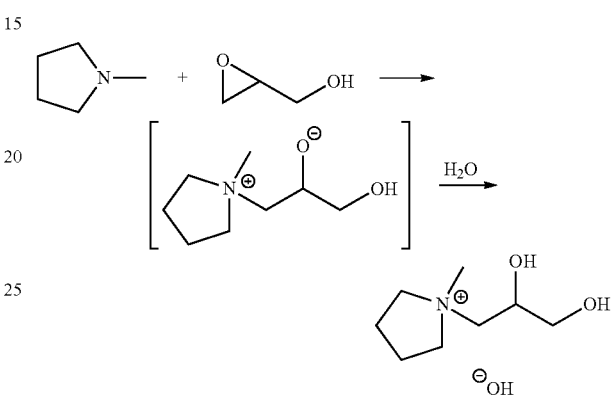

Into a polypropylene reaction vessel is weighed 20.16 g (0.237 moles) of N-methylpyrrolidine and 36.57 g of methanol. To this solution is added by syringe 20 mL of a methanolic solution of 9.51 g glycidol (0.123 moles, based on 96% assay). The rate of addition is adjusted to maintain the temperature at or below 30.5° C. When addition of the glycidol solution is completed, the temperature slowly begins to drop. The solution is stirred for an additional 45 minutes, during which time the internal temperature drops approximately 7° C.

At this point, the internal temperature is approximately at ambient. A methanol solution containing 6.67 g H$_2$O (0.370 moles, 15 mL total volume) is added at a constant rate by syringe over 30 minutes, during which time a slight exotherm is noted. Analysis of this solution before removal of solvent and excess N-methylpyrrolidine reveals hydroxide concentration of 1.0 mol/kg (target 1.2 mol/kg). The quaternary ammonium hydroxide of this Example is a new composition of matter.

EXAMPLE 6

A portion of the methanol solution obtained in Example 5 (approximately 10.08 g, containing 1.01×$10^{-2}$ moles of the quaternary ammonium hydroxide) is placed in a 50 mL polypropylene centrifuge tube and evaporated under a stream of dry nitrogen at ambient temperature over 24 hours to a viscous yellow oil. The tube containing this viscous oil is placed in a vacuum chamber to remove the last traces of solvent and excess N-methylpyrrolidine, yielding 2.14 g of neat quaternary ammonium hydroxide.

Pure DMSO (21.96 g) is added to the tube to bring the total mass to 24.10 g. The tube is gently agitated using a wrist action shaker. After about 15 minutes all solids are dissolved to yield a clear, slightly yellow solution. Analysis of this solution by titration reveals a hydroxide concentration of 0.41 mol/kg (approximately 98% of target concentration of 0.42 mol/kg). Water content by Karl-Fischer titration is zero. This dry, concentrated solution is effective in removing Novolac photoresist from wafer coupons that have been baked at 155° C. for 4 hours. Under the same conditions, pure DMSO is found to be ineffective in removing this baked Novolac film.

The following table includes examples of substituents for $R^1$, $R^2$, $R^3$ and $R^4$, as defined herein. Some of the compounds are known compositions of matter, although none are believed known for use in a process as disclosed and claimed in the present application. Where $R^2$ and $R^3$ or $R^2$, $R^3$ and $R^4$ are combined to form a cyclic or bicyclic structure, the missing element is the quaternary nitrogen atom in the general formula (I) as described herein.

In general formula (I):

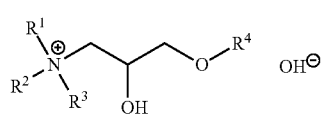

(I)

the following exemplary substituents may be substituted for $R^1$, $R^2$, $R^3$, and $R^4$, in accordance with the present invention, as described herein:

| $R^1$ | $R^2$ | $R^3$ | $R^4$ |
|---|---|---|---|
| Me | Me | Me | H |
| Me | Me | Et | H |
| Me | Me | n-Pr | H |
| Me | Me | i-Pr | H |
| Me | Me | n-Bu | H |
| Me | Me | i-Bu | H |
| Me | Me | sec-Bu | H |
| Me | Me | tert-Bu | H |
| Me | Me | 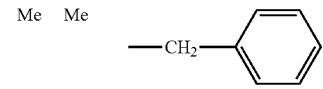 | H |
| Me | Me | —$C_5H_{11}$ | H |
| Me | Me | —$C_6H_{13}$ | H |
| Me | Me | —$C_7H_{15}$ | H |
| Me | Me | —$C_8H_{17}$ | H |
| Me | Me | —$C_9H_{19}$ | H |
| Me | Me | —$C_{10}H_{21}$ | H |
| Me | Me | —$C_{11}H_{23}$ | H |
| Me | Me | —$C_{12}H_{25}$ | H |
| Me | Me | —$C_{13}H_{27}$ | H |
| Me | Me | —$C_{14}H_{29}$ | H |
| Me | Me | —$C_{15}H_{31}$ | H |
| Me | Me | —$C_{16}H_{33}$ | H |
| Me | Me | —$C_{17}H_{35}$ | H |
| Me | Me | —$C_{18}H_{37}$ | H |
| Me | Me | Me | Me |
| Me | Me | Me | Me |
| Me | Me | Et | Me |
| Me | Me | n-Pr | Me |
| Me | Me | i-Pr | Me |
| Me | Me | n-Bu | Me |
| Me | Me | i-Bu | Me |
| Me | Me | sec-Bu | Me |
| Me | Me | tert-Bu | Me |
| Me | Me | —CH$_2$C$_6$H$_5$ | Me |
| Me | Me | —$C_5H_{11}$ | Me |
| Me | Me | —$C_6H_{13}$ | Me |
| Me | Me | —$C_7H_{15}$ | Me |
| Me | Me | —$C_8H_{17}$ | Me |
| Me | Me | —$C_9H_{19}$ | Me |
| Me | Me | —$C_{10}H_{21}$ | Me |
| Me | Me | —$C_{11}H_{23}$ | Me |
| Me | Me | —$C_{12}H_{25}$ | Me |
| Me | Me | —$C_{13}H_{27}$ | Me |
| Me | Me | —$C_{14}H_{29}$ | Me |
| Me | Me | —$C_{15}H_{31}$ | Me |
| Me | Me | —$C_{16}H_{33}$ | Me |
| Me | Me | —$C_{17}H_{35}$ | Me |
| Me | Me | —$C_{18}H_{37}$ | Me |
| Me | Me | Me | Et |
| Me | Me | Et | Et |
| Me | Me | n-Pr | Et |
| Me | Me | i-Pr | Et |
| Me | Me | n-Bu | Et |
| Me | Me | i-Bu | Et |
| Me | Me | sec-Bu | Et |
| Me | Me | tert-Bu | Et |
| Me | Me | —CH$_2$C$_6$H$_5$ | Et |
| Me | Me | —$C_5H_{11}$ | Et |
| Me | Me | —$C_6H_{13}$ | Et |
| Me | Me | —$C_7H_{15}$ | Et |
| Me | Me | —$C_8H_{17}$ | Et |
| Me | Me | —$C_9H_{19}$ | Et |
| Me | Me | —$C_{10}H_{21}$ | Et |
| Me | Me | —$C_{11}H_{23}$ | Et |
| Me | Me | —$C_{12}H_{25}$ | Et |
| Me | Me | —$C_{13}H_{27}$ | Et |
| Me | Me | —$C_{14}H_{29}$ | Et |
| Me | Me | —$C_{15}H_{31}$ | Et |
| Me | Me | —$C_{16}H_{33}$ | Et |
| Me | Me | —$C_{17}H_{35}$ | Et |
| Me | Me | —$C_{18}H_{37}$ | Et |
| Me | Me | Me | n-Pr |
| Me | Me | Et | n-Pr |
| Me | Me | n-Pr | n-Pr |
| Me | Me | i-Pr | n-Pr |
| Me | Me | n-Bu | n-Pr |
| Me | Me | i-Bu | n-Pr |
| Me | Me | sec-Bu | n-Pr |
| Me | Me | tert-Bu | n-Pr |
| Me | Me | —CH$_2$C$_6$H$_5$ | n-Pr |
| Me | Me | —$C_5H_{11}$ | n-Pr |
| Me | Me | —$C_6H_{13}$ | n-Pr |
| Me | Me | —$C_7H_{15}$ | n-Pr |
| Me | Me | —$C_8H_{17}$ | n-Pr |
| Me | Me | —$C_9H_{19}$ | n-Pr |
| Me | Me | —$C_{10}H_{21}$ | n-Pr |
| Me | Me | —$C_{11}H_{23}$ | n-Pr |
| Me | Me | —$C_{12}H_{25}$ | n-Pr |
| Me | Me | —$C_{13}H_{27}$ | n-Pr |
| Me | Me | —$C_{14}H_{29}$ | n-Pr |
| Me | Me | —$C_{15}H_{31}$ | n-Pr |
| Me | Me | —$C_{16}H_{33}$ | n-Pr |
| Me | Me | —$C_{17}H_{35}$ | n-Pr |
| Me | Me | —$C_{18}H_{37}$ | n-Pr |
| Me | Me | Me | i-Pr |
| Me | Me | Et | i-Pr |
| Me | Me | n-Pr | i-Pr |
| Me | Me | i-Pr | i-Pr |
| Me | Me | n-Bu | i-Pr |
| Me | Me | i-Bu | i-Pr |
| Me | Me | sec-Bu | i-Pr |
| Me | Me | tert-Bu | i-Pr |

| R¹ | R² | R³ | R⁴ |
|---|---|---|---|
| Me | Me | —CH₂—Ph | i-Pr |
| Me | Me | —C₅H₁₁ | i-Pr |
| Me | Me | —C₆H₁₃ | i-Pr |
| Me | Me | —C₇H₁₅ | i-Pr |
| Me | Me | —C₈H₁₇ | i-Pr |
| Me | Me | —C₉H₁₉ | i-Pr |
| Me | Me | —C₁₀H₂₁ | i-Pr |
| Me | Me | —C₁₁H₂₃ | i-Pr |
| Me | Me | —C₁₂H₂₅ | i-Pr |
| Me | Me | —C₁₃H₂₇ | i-Pr |
| Me | Me | —C₁₄H₂₉ | i-Pr |
| Me | Me | —C₁₅H₃₁ | i-Pr |
| Me | Me | —C₁₆H₃₃ | i-Pr |
| Me | Me | —C₁₇H₃₅ | i-Pr |
| Me | Me | —C₁₈H₃₇ | i-Pr |
| Me | Me | Me | n-Bu |
| Me | Me | Et | n-Bu |
| Me | Me | n-Pr | n-Bu |
| Me | Me | i-Pr | n-Bu |
| Me | Me | n-Bu | n-Bu |
| Me | Me | i-Bu | n-Bu |
| Me | Me | sec-Bu | n-Bu |
| Me | Me | tert-Bu | n-Bu |
| Me | Me | —CH₂—Ph | n-Bu |
| Me | Me | Me | Ph |
| Me | Me | Et | Ph |
| Me | Me | n-Pr | Ph |
| Me | Me | i-Pr | Ph |
| Me | Me | n-Bu | Ph |
| Me | Me | i-Bu | Ph |
| Me | Me | sec-Bu | Ph |
| Me | Me | tert-Bu | Ph |
| Me | Me | —CH₂—Ph | Ph |
| Me | Me | Me | —C₆H₄—OMe |
| Me | Me | Et | —C₆H₄—OMe |
| Me | Me | n-Pr | —C₆H₄—OMe |
| Me | Me | i-Pr | —C₆H₄—OMe |
| Me | Me | n-Bu | —C₆H₄—OMe |
| Me | Me | i-Bu | —C₆H₄—OMe |
| Me | Me | sec-Bu | —C₆H₄—OMe |
| Me | Me | tert-Bu | —C₆H₄—OMe |
| Me | Me | —CH₂—Ph | —C₆H₄—OMe |
| Me | | cyclopentyl | i-Pr |
| Me | | cyclohexyl | i-Pr |
| Me | | tetrahydropyranyl (O) | i-Pr |
| Me | | piperidinyl (N) | i-Pr |
| Me | | bicyclic alkyl | i-Pr |
| Me | | DABCO-like (N) | i-Pr |
| Me | | N⁺-methyl DABCO | i-Pr |
| | | isopropoxy-hydroxy-propyl-N⁺(DABCO) | i-Pr |

In the foregoing table, in all cases in which any R¹, R², R³ or R⁴ group is defined as C₅H₁₁—C₁₈H₃₇ alkyl, the alkyl group may be linear or branched.

It should be appreciated that the process steps and compositions described herein may not form a complete system or process flow for carrying out a method for removing a residue from a substrate, such as would be used in actual practice. The present invention can be practiced in conjunction with synthetic organic and residue removal techniques and apparatus currently used in the art, and only so much of the commonly practiced materials, apparatus and process steps are included as are necessary for an understanding of the present invention.

While the principles of the invention have been explained in relation to certain particular embodiments, and are provided for purposes of illustration, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A composition of matter, wherein the composition comprises:
a quaternary ammonium hydroxide having a general formula (I):

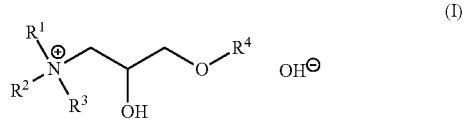

wherein in the general formula (I):
$R^1$ may be $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or $R^1$ may have the following general formulae (i) or (ii):

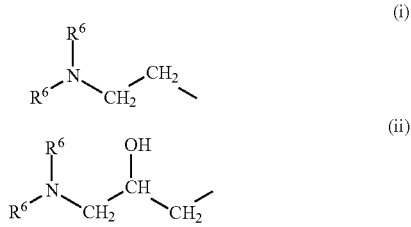

wherein in general formulae (i) and (ii), $R^6$ is independently $C_1$-$C_4$ branched or unbranched alkyl,
$R^2$ and $R^3$ may be independently $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or
$R^1$ is as defined above, and $R^2$ and $R^3$ may together form a heterocyclic ring containing the quaternary ammonium N atom of the general formula (I) and 4 to 7 carbon atoms, or
$R^1$ is as defined above, and $R^2$ and $R^3$ may together form a heterocyclic ring containing the quaternary ammonium nitrogen atom of the general formula (I), and either a second nitrogen atom or an oxygen atom and 3 to 6 carbon atoms, wherein the second nitrogen atom may be substituted with one or two groups independently selected from $C_1$-$C_{18}$ linear or branched alkyl, $C_2$-$C_{18}$ linear or branched alkanol, $C_3$-$C_{18}$ linear or branched polyol, benzyl, or substituted benzyl, wherein when present, substituted benzyl is substituted with one or more of $C_1$-$C_4$ alkyl, $C_1$-$C_4$ alkoxy, or halogen, or
$R^1$, $R^2$, and $R^3$ together may form a bicyclic structure containing from two to four carbon atoms between first and second bridgehead positions, wherein the quaternary N atom of the general formula (I) is at the first bridgehead position, and a carbon or a tertiary or quaternary nitrogen is at the second bridgehead position, wherein when the second bridgehead position is a carbon or a quaternary nitrogen, the carbon or quaternary nitrogen is substituted with $R^5$, in which $R^5$ is H or a $C_1$-$C_4$ branched or unbranched alkyl group, and
$R^4$ is $C_1$-$C_{18}$ linear or branched alkyl, phenyl or substituted phenyl, or benzyl or substituted benzyl, wherein when present, substituted phenyl or substituted benzyl is substituted with one or more of $C_1$-$C_4$ alkyl, $C_1$-$C_4$ alkoxy, or halogen, with the provisos that, if $R^4$ is mono-substituted phenyl, the substituent is other than a 4-fluoro or a 4-alkyl group; and if $R^4$ is di-substituted phenyl, the di-substituted phenyl is other than 2,5-dimethylphenyl.

2. The composition of claim 1 wherein the quaternary ammonium hydroxide has general formula (II):

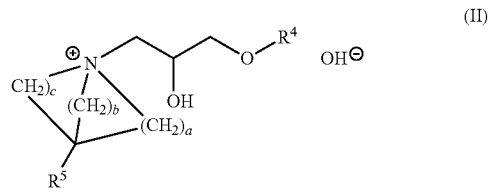

wherein, in general formula (II), each of a, b and c are independently 2-4, $R^5$ is H or a $C_1$-$C_4$ branched or unbranched alkyl.

3. The composition of claim 1 wherein the quaternary ammonium hydroxide has general formula (III):

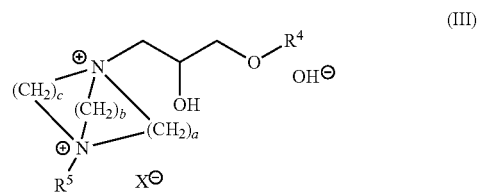

wherein, in general formula (III), each of a, b and c are independently 2-4, $R^5$ is a $C_1$-$C_4$ branched or unbranched alkyl, and X is a halide or OH.

4. The composition of claim 1 wherein the quaternary ammonium hydroxide has general formula (IV):

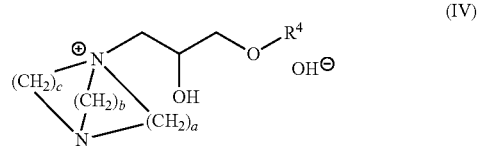

wherein in general formula (IV), each of a, b and c are independently 2-4.

* * * * *